(12) United States Patent
Morlet (10) Patent No.: US 8,568,422 B2
(45) Date of Patent: Oct. 29, 2013

(54) CUTTING NEEDLE TIP FOR SURGICAL INSTRUMENT

(76) Inventor: Nigel Morlet, Mosman Park (AU)

( * ) Notice: Subject to any disclaimer, the term of this patent is extended or adjusted under 35 U.S.C. 154(b) by 142 days.

(21) Appl. No.: 13/061,667

(22) PCT Filed: Aug. 28, 2009

(86) PCT No.: PCT/AU2009/001109
§ 371 (c)(1),
(2), (4) Date: Apr. 6, 2011

(87) PCT Pub. No.: WO2010/022460
PCT Pub. Date: Mar. 4, 2010

(65) Prior Publication Data
US 2011/0208114 A1 Aug. 25, 2011

(30) Foreign Application Priority Data
Sep. 1, 2008 (AU) ................ 2008904517

(51) Int. Cl.
*A61F 9/007* (2006.01)
(52) U.S. Cl.
USPC .......................... 606/107; 606/170
(58) Field of Classification Search
USPC ......... 606/106, 107, 167, 169, 170, 185, 187, 606/188; 604/22, 27, 35, 44, 187, 239
See application file for complete search history.

(56) References Cited

U.S. PATENT DOCUMENTS

| | | | |
|---|---|---|---|
| 2,711,733 A | 8/1951 | Jacoby, Jr. | |
| 2,828,744 A | 4/1958 | Hirsch et al. | |
| 3,071,135 A | 1/1963 | Baldwin et al. | |
| 3,173,200 A | 3/1965 | Dunmire et al. | |
| 3,589,363 A | 6/1971 | Banko | |
| 4,490,139 A | 12/1984 | Huizenga et al. | |
| 4,561,445 A | 12/1985 | Berke et al. | |
| 4,689,040 A | 8/1987 | Thompson | |

(Continued)

FOREIGN PATENT DOCUMENTS

| DE | 196 28 252 | 1/1998 |
|---|---|---|
| DE | 199 42 693 | 3/2001 |

(Continued)

OTHER PUBLICATIONS

International-Type Search Report issued in National Application No. 2008904517, mailed Oct. 27, 2008—2 pages.

(Continued)

*Primary Examiner* — Elizabeth Houston
(74) *Attorney, Agent, or Firm* — Hamre, Schumann, Mueller & Larson, P.C.

(57) ABSTRACT

A needle 20 for use with a torsional or transverse ultrasound surgical phacoemulsification instrument comprises a hollow elongated needle body 22 having a needle tip 24 at a distal end for cutting lens material. The needle tip 24 is flared in one plane to produce a substantially elliptical tip mouth 26. The elliptical tip mouth 26 has a major axis 'X' larger than an outer diameter of the needle body and a minor axis 'Y' smaller than the major axis so as to form a spade-shaped tip. The eccentricity of the elliptical tip mouth 26 can be varied, however for practical purposes it is preferred that the major axis of the tip mouth is about 1.5 to 2.5 times longer than the minor axis. The spade-shaped tip 24 provides an improved cutting action, particularly with torsional ultrasonic vibration, the cutting action being analogous to that of a spade drill bit used in woodworking.

29 Claims, 6 Drawing Sheets (56) References Cited

U.S. PATENT DOCUMENTS

| | | |
|---|---|---|
| 4,889,529 A | 12/1989 | Haindl |
| 4,959,049 A | 9/1990 | Smirmaul |
| 5,162,044 A | 11/1992 | Gahn et al. |
| 5,354,537 A | 10/1994 | Moreno |
| 5,515,871 A | 5/1996 | Bittner et al. |
| 5,653,724 A | 8/1997 | Imonti |
| 5,725,495 A | 3/1998 | Strukel et al. |
| 5,733,266 A | 3/1998 | Gravlee, Jr. |
| 5,788,679 A | 8/1998 | Gravlee, Jr. |
| 5,938,635 A | 8/1999 | Kuhle |
| 5,968,022 A | 10/1999 | Saito |
| 5,993,408 A | 11/1999 | Zaleski |
| 5,997,499 A | 12/1999 | Sussman et al. |
| 6,007,555 A | 12/1999 | Devine |
| 6,159,175 A | 12/2000 | Strukel et al. |
| 6,165,150 A | 12/2000 | Banko |
| 6,283,974 B1 | 9/2001 | Alexander |
| 6,299,591 B1 | 10/2001 | Banko |
| 6,398,759 B1 | 6/2002 | Sussman et al. |
| 6,533,750 B2 | 3/2003 | Sutton et al. |
| 2002/0156492 A1 | 10/2002 | Timm et al. |
| 2004/0193121 A1 | 9/2004 | Kadziauskas et al. |
| 2004/0215206 A1 | 10/2004 | Kadziauskas et al. |
| 2005/0020990 A1 | 1/2005 | Akahoshi |
| 2006/0052758 A1 | 3/2006 | Dewey |
| 2006/0217672 A1 | 9/2006 | Chon |
| 2006/0253056 A1 | 11/2006 | Kadziauskas et al. |
| 2007/0260199 A1 | 11/2007 | Rockley |
| 2008/0058708 A1 | 3/2008 | Akahoshi |
| 2008/0139994 A1 | 6/2008 | Mackool et al. |
| 2008/0188792 A1 | 8/2008 | Barrett |
| 2009/0099536 A1 | 4/2009 | Akahoshi |
| 2009/0137971 A1 | 5/2009 | Akahoshi |
| 2009/0192440 A1 | 7/2009 | Akahoshi |

FOREIGN PATENT DOCUMENTS

| | | |
|---|---|---|
| EP | 0 962 205 | 12/1999 |
| EP | 1 464 310 | 10/2004 |
| EP | 1 532 996 | 5/2005 |
| JP | 2006-000644 | 1/2006 |
| JP | 2008-154842 | 7/2008 |
| JP | 2008-154843 | 7/2008 |
| WO | 94/22402 | 10/1994 |
| WO | 00/74615 | 12/2000 |
| WO | 2005/025434 | 3/2005 |
| WO | 2005/032439 | 4/2005 |
| WO | 2007/119107 | 10/2007 |
| WO | 2008/147771 | 12/2008 |
| WO | 2009/000959 | 12/2008 |

OTHER PUBLICATIONS

International-Type Search Report issued in National Application No. 2010901302, mailed Jul. 1, 2010—2 pages.

International-Type Search Report issued in National Application No. 2010901302, mailed Aug. 12, 2010—2 pages.

International Search Report issued in International Application No. PCT/AU2009/001109, mailed Oct. 28, 2009—5 pages.

Prior Art

CUTTING NEEDLE TIP FOR SURGICAL INSTRUMENT

FIELD OF THE INVENTION

The present invention relates to an improved needle tip for a surgical instrument and relates particularly, though not exclusively, to a needle tip for an ultrasonic surgical instrument of the kind used for phacoemulsification in surgical cataract removal procedures.

BACKGROUND TO THE INVENTION

Ophthalmologists have developed surgical cataract removal procedures which involve removal of the crystalline lens and replacement with an artificial lens through a small incision in the capsular bag in which the lens material is contained. Charles Kelman and Anton Banko were among the first to successfully develop a technique for removal of cataracts using a handheld surgical instrument with a hollow needle vibrating at ultrasonic frequencies. U.S. Pat. No. 3,589,363 describes their ground-breaking technique. This technique, which has become known as phacoemulsification, involves inserting a needle tip vibrating at ultrasonic frequencies into the eye through a small corneal incision. As the vibrating needle tip and ultrasonic wave contacts the lens material it disintegrates and emulsifies it with an irrigating fluid. A coaxial sleeve over the needle or a second canula delivers the irrigating fluid, and the disintegrated lens disperses to form an emulsion which is aspirated through the hollow interior of the needle.

Depending on the extent of the cataract formation the diseased lens material can vary considerably in hardness and/or density. The harder or more dense the diseased material the more difficult it is to remove using phacoemulsification. Various types of ultrasonic vibration have been tried to improve the rate and efficiency of emulsification; previously using longitudinal alone, but recently using transverse and torsional vibration, as well as combinations thereof. In addition, many have developed alternative needle and tip configurations to try to improve on the standard round needle with a bevelled tip. For example, tips that are flared to produce an "acoustic horn" to focus the ultrasonic sound waves. Yet other examples use transverse steps, or "baffles", or concave recesses within the mouth of the tip to enhance cavitation and emulsification.

The effect of these tip modifications with transverse or torsional ultrasound is limited because the designs were principally for longitudinal movement of the needle. The standard round tip on a straight needle does not work with torsional ultrasound handpieces, so the bent needle that Kelman developed is used. However this type of bent needle has poor ergonomics and can be difficult to use during phacoemulsification surgery. Because of poor tip efficiency, it is also easily blocked with incompletely emulsified lens material.

The present invention was developed with a view to providing an improved needle tip configuration principally for torsional and transverse ultrasonic handpieces to provide better phacoemulsification efficiency (i.e. puts less energy into the eye, reducing any thermal side effects), especially with a straight needle, whilst maintaining good fluid extraction of emulsified fragments (fluidics). It will be appreciated that the same type of needle tip may also be use for other types of surgical procedure such as removal of tumours (e.g. brain tumours), liposuction, or in dentistry. Therefore the invention is not limited in its application to phacoemulsification.

References to prior art in this specification are provided for illustrative purposes only and are not to be taken as an admission that such prior art is part of the common general knowledge in Australia or elsewhere.

SUMMARY OF THE INVENTION

According to one aspect of the present invention there is provided a needle for a surgical instrument for removal of diseased or unwanted tissue, the needle comprising:

a hollow elongate needle body having a needle tip at a distal end for cutting tissue, the needle tip being flared in one plane to produce a substantially elliptical tip mouth with a major axis larger than an outer diameter of the needle body and a minor axis smaller than the major axis so as to form a somewhat shallow curved "spade-shaped" tip.

Preferably the major axis of the tip mouth is about 1.5 to 2.5 times longer than the minor axis. Preferably the minor axis is approximately equal to the diameter of the needle body. Preferably the spade-shaped tip has a central longitudinal axis (the tip axis) which is substantially aligned with a central longitudinal axis of the needle body.

Preferably the tip mouth has a lip which is angled with respect to the tip axis. Advantageously the tip mouth has a first lip portion which is angled in one direction with respect to the tip axis and a second lip portion which is angled in the opposite direction with respect to the tip axis. Preferably the first lip portion of the tip mouth is angled with respect to the tip axis to a different degree than the second lip portion.

In some embodiments the first and second lip portions of the tip mouth both lie in a respective substantially flat plane. Typically the plane of the first lip portion of the tip mouth is angled at between 90° to 45° to the tip axis, and the plane of the second portion of the tip mouth is angled at between 90° to 45° to the tip axis. In one embodiment the plane of the first lip portion is angled at 90° to the tip axis and the plane of the second lip portion is angled at about 60° to the tip axis. In another embodiment the plane of the first lip portion is angled at 60° to the tip axis and the plane of the second lip portion is angled at about 60° to the tip axis.

In an alternate embodiment the first and second lip portions of the tip mouth are both substantially arcuate in profile. Typically the angle of curvature of both the first and second arcuate lip portions is substantially the same.

In one embodiment a plane which passes through the line where the two lip portions meet is substantially aligned with the tip axis. In another embodiment the plane which passes through the line where the two lip portions meet is offset from the tip axis.

Preferably the lip of the tip mouth has a bevelled edge, providing a sharper cutting edge to the lip.

Preferably the surface of the lip of the tip of the mouth is not smooth, and roughened to create a "serrated" edge.

Preferably the internal surface of the tip of the mouth is not smooth and is roughened to the lip of the tip, substantially in the direction of the tip axis.

According to a second aspect of the present invention there is provided a needle for a surgical instrument for removal of diseased or unwanted tissue, the needle comprising:

a hollow elongate needle body having a needle tip at a distal end for cutting tissue, the needle tip having a tip mouth with a lip, the lip of the tip mouth having a bevelled edge providing a sharper cutting edge to the lip.

Preferably both the bevel orientation and the bevel angle changes around the circumference of the lip. Preferably the bevelled edge of the tip mouth changes from an outside bevel to an inside bevel around the circumference of the tip mouth. Preferably the needle tip is flared in one plane to produce a substantially elliptical tip mouth with a major axis larger than an outer diameter of the needle body and a minor axis approximately equal to the diameter of the needle body so as to form a somewhat shallow curved "spade-shaped" tip. Typically the change in the orientation of the bevel is at the intersection of the major and minor axes and the circumference of the tip mouth.

Preferably when the spade-shaped tip has a mouth with a lip that is angled with respect to the tip axis, the orientation of the bevelled edge changes from the inside to the outside at the intersection of the angle.

Preferably the surface of the lip of the tip of the mouth is not smooth, and roughened to create a "serrated" edge.

Preferably an internal surface of the tip is not smooth and is roughened to a lip of the tip mouth substantially in the direction of the tip axis.

According to a third aspect of the present invention there is provided a needle for a surgical instrument for removal of diseased or unwanted tissue, the needle comprising:

a hollow elongate needle body having a needle tip at a distal end for cutting tissue, wherein an internal surface of the needle tip is not smooth and is roughened adjacent the tip mouth substantially in the direction of a longitudinal axis of the tip (the tip axis).

Preferably the tip mouth has a lip and the surface of the lip of the tip of the mouth is not smooth, and is roughened to create a "serrated" edge.

Preferably the internal surface of the tip is grooved in the general direction of the tip axis. Preferably the grooves extend to the lip of the tip mouth creating a "serrated" edge to the lip. Preferably the grooves extend from the lip of the mouth, along the internal surface of the tip, to the neck of the needle body. Advantageously the grooves spiral along the internal surface towards the neck of the needle body.

Advantageously the grooves have a sharp profile on one or both edges.

Preferably the grooves are mostly square or triangular in profile. Alternatively the grooves are mostly rounded in profile, or sharp on one edge and rounded on the other. The grooves may optionally be asymmetric about the tip axis.

Throughout the specification, unless the context requires otherwise, the word "comprise" or variations such as "comprises" or "comprising", will be understood to imply the inclusion of a stated integer or group of integers but not the exclusion of any other integer or group of integers. Likewise the word "preferably" or variations such as "preferred", will be understood to imply that a stated integer or group of integers is desirable but not essential to the working of the invention.

BRIEF DESCRIPTION OF THE DRAWINGS

The nature of the invention will be better understood from the following detailed description of several specific embodiments of a needle for a surgical instrument, given by way of example only, with reference to the accompanying drawings, in which:

FIGS. 1 (a) & (b) show a prior art needle tip, and (c) a Kelman modification of a prior art needle tip;

FIG. 2 (a) is a side view of a first embodiment of a needle tip in accordance with the present invention;

FIG. 2 (b) is a top plan view of the needle tip of FIG. 2 (a);

FIG. 2 (c) is a top perspective view of the needle tip of FIG. 2 (a);

FIGS. 2 (d) and (e) are details of the lip of the needle tip shown in FIG. 2 (c);

FIG. 3 (a) is a side view of a second embodiment of a needle tip in accordance with the present invention;

FIG. 3 (b) is a top plan view of the needle tip of FIG. 3 (a);

FIG. 3 (c) is a detailed view of the lip of the needle tip of FIG. 3 (b);

FIG. 3 (d) is a top perspective view of the needle tip of FIG. 3 (a);

FIG. 3 (e) is a detailed view of the lip of the needle tip shown in FIG. 3 (d);

DETAILED DESCRIPTION OF PREFERRED EMBODIMENTS

Figure 1A:
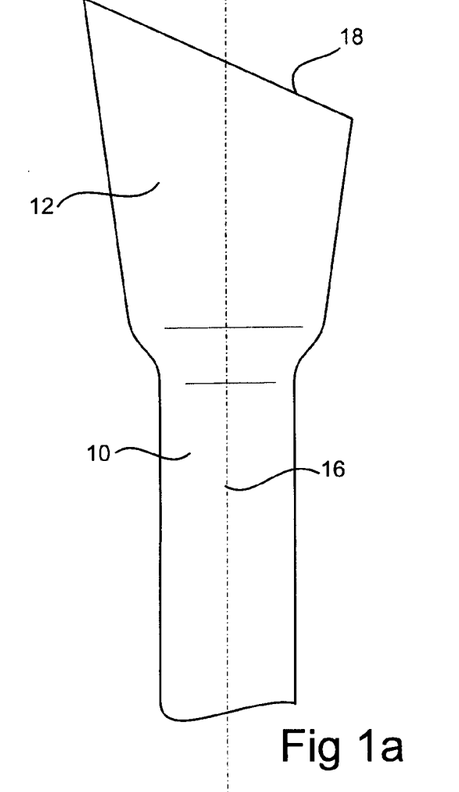
Figure 1B:
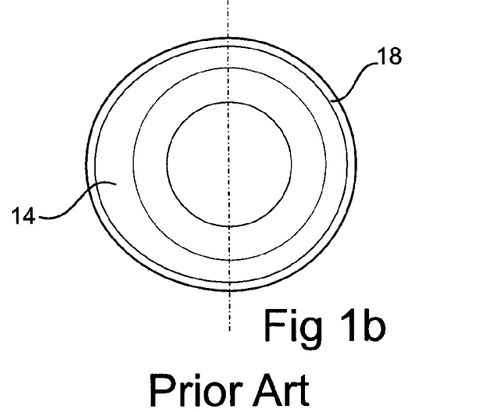

FIG. 1 illustrates a prior art needle of the kind used with a longitudinal ultrasonic handpiece (phacoemulsification probe) for surgically removing a cataract lens. It has a needle body 10 with a needle tip 12 at its distal end that engages with the crystalline lens. As can be seen most clearly in FIG. 1 (b) the mouth 14 of the tip 12 is of circular shape and is concentric with a central longitudinal axis 16 of the needle body 10. A lip 18 of the mouth 14 lies in a substantially flat plane which is angled in one direction with respect the longitudinal axis 16 of the needle body. The original phacoemulsification probe (not illustrated) employed longitudinal ultrasonic vibration of the needle tip 12 to disintegrate and emulsify the lens tissue.

Figure 1C:
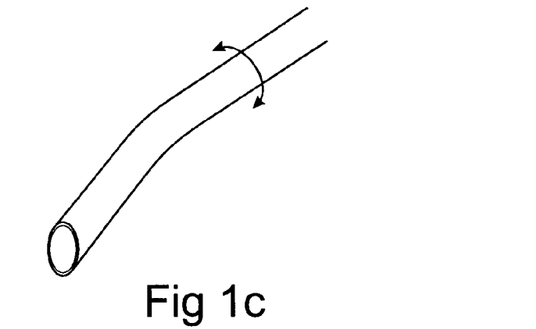

A problem with this type of prior art tip is that torsional ultrasonic vibration, which moves the tip 12 about the longitudinal axis 16, does not provide much, if any, cutting action. The vibration also tends to produce localised heating due to friction with the surrounding tissue, compounded by blockage of the tip and flow restriction due to inefficient disintegration and emulsification of the cataract lens. A prior art Kelman style modification, where the standard needle has a bent shaft to offset the tip as shown in FIG. 1c, is typically used for torsional phacoemulsification. This style of needle tip produces a "scything" action when vibrated by a torsional or transverse ultrasonic handpiece. However there are problems with using this type of tip during phacoemulsification surgery as noted above.

A preferred embodiment of a needle 20 in accordance with the invention as illustrated in FIG. 2, for use with a torsional or transverse ultrasound surgical instrument, comprises a hollow elongated needle body 22 having a needle tip 24 at a distal end for cutting lens material (not shown). The needle tip 24 is flared in one plane to produce a substantially elliptical tip mouth 26, as can be seen most clearly in FIG. 2 (b). The elliptical tip mouth 26 has a major axis 'X' larger than an outer diameter of the needle body and a minor axis 'Y' approximately equal to the diameter of the needle body so as to form a spade-shaped tip. The minor axis "Y" may be larger than the diameter of the needle body. The eccentricity of the elliptical tip mouth 26 can be varied, however for practical purposes it is preferred that the major axis of the tip mouth is about 1.5 to 2.5 times longer than the minor axis. The spade-shaped tip 24 provides an improved cutting action, particularly with torsional ultrasonic vibration, the cutting action being analogous to that of a spade drill bit used in woodworking.

As can be seen most clearly in FIG. 2 (a) the spade-shaped tip 24 is flared in one plane so as to have a width dimension 'C' nearer to the needle body smaller than the width dimension 'A' further from the needle body. Furthermore the spade-shaped tip 24 preferably has a central longitudinal axis 'T' (hereinafter "the tip axis T") which is substantially aligned with a central longitudinal axis 'N' of the needle body 22 (hereinafter "the needle axis N"). If desired the tip axis T may also be angled with respect to the needle axis N to create a side-to-side sweeping action during torsional phacoemulsification, similar to the Kelman style tip. However it has been found that the shallow curved spade-shaped tip 24 already significantly improves cutting and fluidic efficiency without having an angled tip, since it provides its own "rotatory" cutting action by virtue of its spade-shape.

Figure 2A:
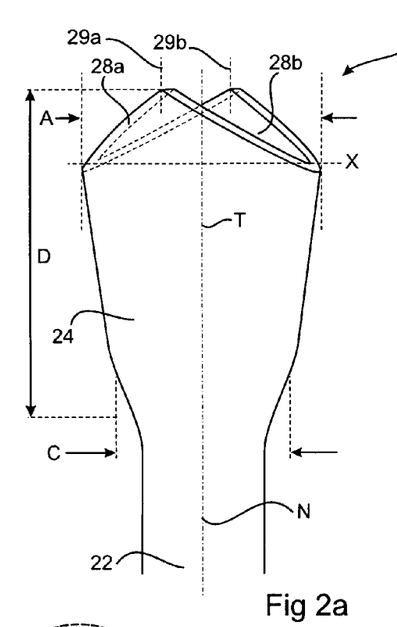

Preferably the spade-shaped tip 24 has a mouth 26 with a lip 28 which is angled with respect to the tip axis T. In this embodiment the mouth 26 of the tip has a first lip portion 28a lying in a plane which is angled in one direction with respect to the tip axis T, and a second lip portion 28 lying in a plane which is angled in the opposite direction with respect to the tip axis T. The first lip portion 28a of the mouth of the tip may lie in a plane which is angled with respect to the tip axis T to a different degree than the angle of the plane of the second lip portion 28b.

In this embodiment the first lip portion 28a and the second lip portion 28b both lie in planes which are also tilted with respect to the major axis X of the tip mouth 26. As shown in FIG. 2 (a) the plane of the first lip portion 28a is tilted downwards away from the viewer and the plane of the second lip portion 28b is tilted downwards towards the viewer. The plane of the first lip portion 28a of the mouth 26 is angled at about 45° to the tip axis T and tilted from about 10° to 45° to the major axis X. The plane of the second lip portion 28b is angled at about 55° to the tip axis T and tilted from about 10° to 45° to the major axis X (but in the opposite direction to the plane of the first lip portion 28a). In this embodiment, because of the tilting of the two planes, the points 29a and 29b where the two lip portions 28 meet are both slightly offset from the tip axis T. The angled planes of the lip portions 28 provide improved visibility for the surgeon at the mouth 26 of the tip 24 during phacoemulsification. The tilting of the two planes directs the ultrasonic radiation (acoustic streaming) out of the mouth 26, at the same time enhancing aspiration into the mouth 26, improving the tip fluidics as well as cutting efficiency.

The tilting of the two planes of the lip portions 28a and 28b also has the effect of giving the lip of the tip mouth 26 a bevelled edge providing a sharper cutting edge to the lip. Advantageously the angle of bevel changes around the circumference of the lip, as shown in the detailed enlargements of FIGS. 2(d) and 2(e). Because of the angle of tilt of the respective planes of the lip portions 28, the bevelled edge of the lip 28 changes from an outside bevel to inside bevel around the circumference of the tip mouth 26. The change in the orientation of the bevel is at the intersection of the major axis X and the circumference of the tip mouth, and at the points 29a and 29b where the two lip portions 28 meet.

Figure 2B:
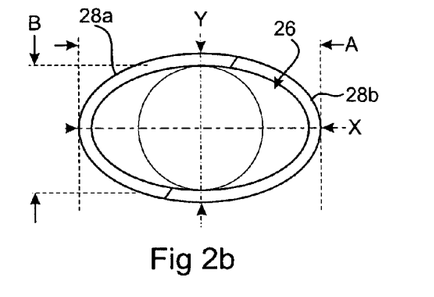
Figures 2C, 2D:
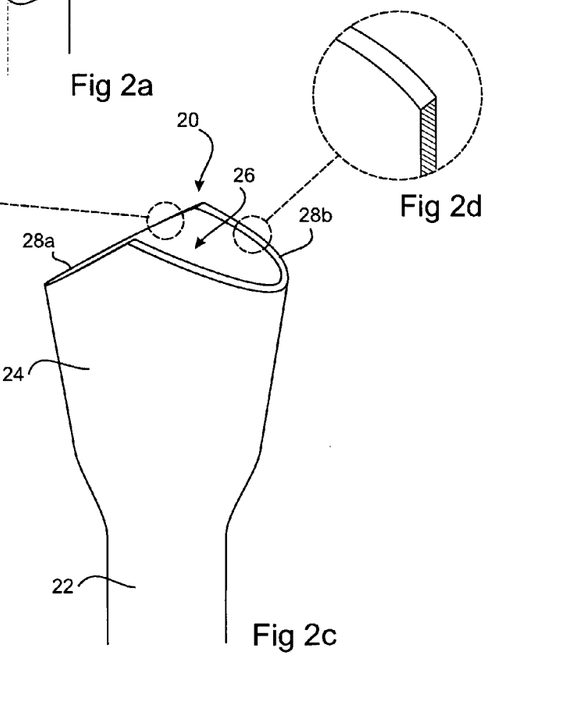
Figure 2E:
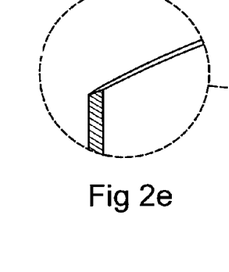

The preferred embodiments of the spade-shaped tip according to the invention are all typically between about 1.6 mm to 2.2 mm in length (D). In the first embodiment of the needle 20, illustrated in FIG. 2, the spade-shaped tip 24 is about 2.0 mm long in its length dimension D. The mouth 26 is about 0.9 mm deep B on its minor axis, and about 1.8 mm wide A on its major axis. The tip 24 is about 1.05 mm wide at C. The walls of the tip (forming the lip) are about 0.15 mm thick.

A second embodiment of the needle 30 for a torsional ultrasound surgical instrument, as illustrated in FIG. 3, is in many respects similar to the first embodiment 20. The needle 30 comprises a hollow elongated needle body 32 having a needle tip 34 at a distal end for cutting lens material (not shown). The needle tip 34 is flared in one plane to produce a substantially elliptical tip mouth 36, as can be seen most clearly in FIG. 3(b). The elliptical tip mouth 36 has a major axis 'X' larger than an outer diameter of the needle body and a minor axis 'Y' approximately equal to the diameter of the needle body so as to form a spade-shaped tip, similar to the first embodiment 20.

As with the previous embodiment, the spade-shaped tip 34 has a tip mouth 36 with a lip 38 which is angled with respect to the tip axis T. The mouth 36 of the tip has a first lip portion 38a lying in a plane which is angled in one direction with respect to the tip axis T, and a second lip portion 38b lying in a plane which is angled in the opposite direction with respect to the tip axis T. However in this embodiment the planes in which the lip portions 38a and 38b lie are not tilted with respect to the major axis of the tip mouth 36. Hence the edge of the lip 38 is substantially orthogonal rather than bevelled. Furthermore, although the two points where the two lip portions 28 meet are both offset to the same side of the tip axis T, they are substantially aligned at 39 when viewed in side elevation, as in FIG. 3(a). Again the offset of the mouth relative to the tip axis T improves the tip fluidics with the torsional movement.

Figure 3A:
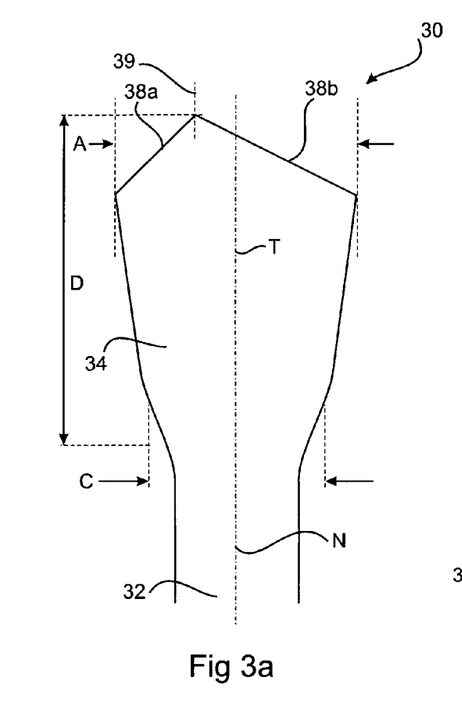

Preferably the surface of the lip of the tip of the mouth is not smooth, and roughened to create a "serrated" edge 39. The serrations are substantially aligned in the direction of the radius from the tip axis T. Alternatively the serrations are angled between 0°-90° to the radius from tip axis T.

Preferably an internal surface of the tip 34 is not smooth but is roughened to the lip 38 of the tip mouth 36 substantially in the direction of the tip axis T. In this embodiment the internal surface of the tip 34 is grooved 37 in the general direction of the tip axis T. Preferably the grooves 37 extend to the lip 38 of the tip mouth creating a "serrated" edge to the lip as shown in FIG. 3(e). The serrated edge of the lip 38 enhances the cutting efficiency of the tip 34, further assisting in the efficient emulsification of the lens material.

Figure 3B:
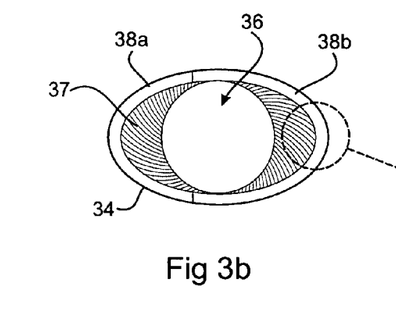
Figure 3C:
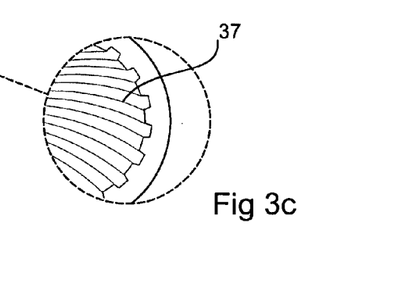
Figure 3D:
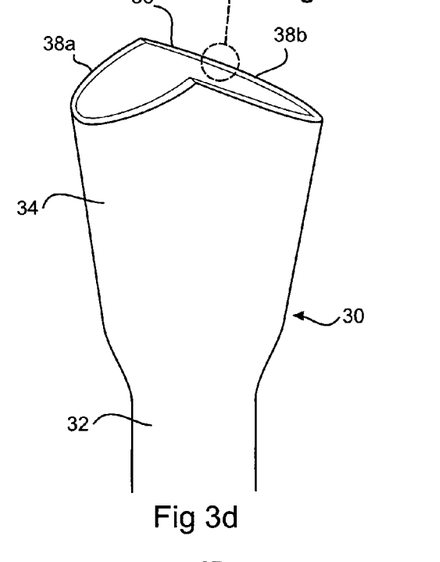
Figure 3E:
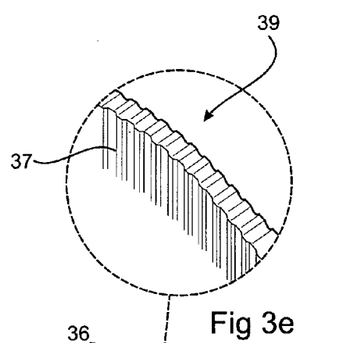

The grooves 37 preferably extend from the lip 38 of the mouth 36, along the internal surface of the tip, to the neck of the needle body 32, as shown in FIG. 3(b). Advantageously the grooves spiral along the internal surface towards the neck of the needle body. The grooves 37 have the effect of 'focussing' the ultrasonic radiation, further enhancing the emulsification with the acoustic streaming. The grooves also "channel" the flow of emulsified lens material debris into the centre of the tip mouth 36 and into the hollow interior of the needle body, thereby enhancing the fluidics of aspiration.

Advantageously the grooves 37 have a sharp profile on one edge. This provides better propagation and reflection of the ultrasonic vibrations. The grooves 37 may also have a sharp profile on both edges. The grooves 37 of this embodiment are mostly square or triangular in profile. Alternatively the grooves may be mostly rounded in profile. The grooves may be symmetric or asymmetric about the tip axis.

Figure 4:
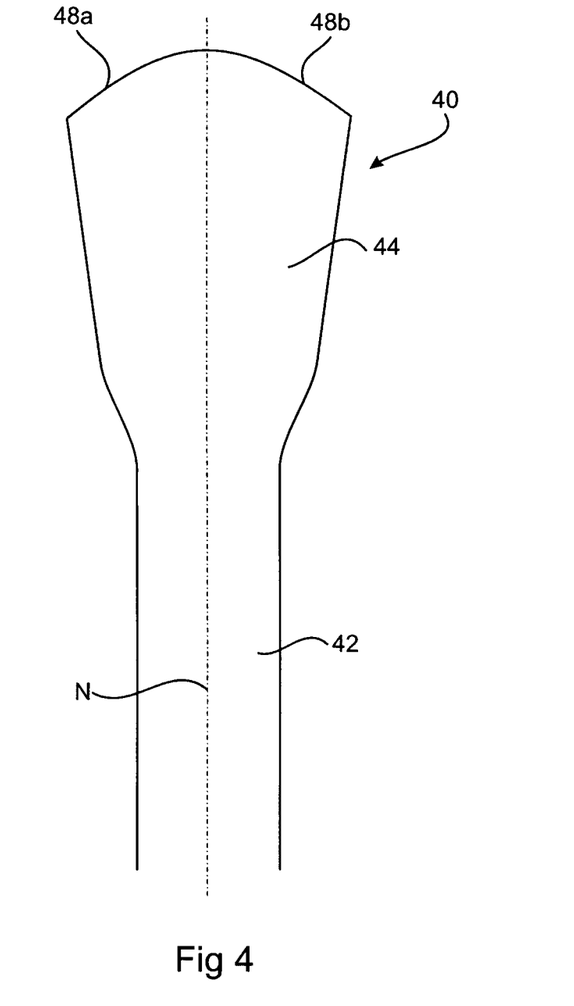
FIG. 4 is a side view of a third embodiment of a needle tip in accordance with the present invention.

A third embodiment of the needle 40 for a surgical instrument in accordance with the invention, as illustrated in FIG. 4, is similar to the first and second embodiments 20 and 30 and therefore will not be described again in detail. The needle 40 has a needle body 42 and a spade-shaped needle tip 44. The needle tip 44 is flared in one plane to produce a substantially elliptical tip mouth, with a major axis larger than an outer diameter of the needle body 42 and a minor axis smaller than the major axis so as to form the spade-shaped tip 44.

In this embodiment the mouth (not visible) of the spade-shaped tip 44 has a lip 48 which is arcuate in profile. The lip 48 has a first arcuate lip portion 48a which is angled in one direction with respect to the tip axis T and a second arcuate lip portion 48b which is angled in the opposite direction with respect to the tip axis T. In this embodiment both the first and second arcuate lip portions 48a and 48b have a substantially identical degree of curvature and therefore the lip 48 is symmetrical about the tip axis T with a parabola-shaped profile. A top plan view of the spade-shaped tip 44 would be similar to that shown in FIG. 2 (b). In other respects the spade-shaped tip 44 may be substantially identical to the first embodiment 24 and tip 34 of the second embodiment.

Although the needle tip 44 of this embodiment is formed with a lip 48 having a convex profile, a similar elliptically shaped mouth may be achieved by making the first and second lip portions 48a and 48b a shallow concave arcuate profile. The first lip portion 48a and of the second lip portion 48b would both be angled at much the same angle of between 60° and 45° to the tip axis T, but in opposite directions.

Figure 5:
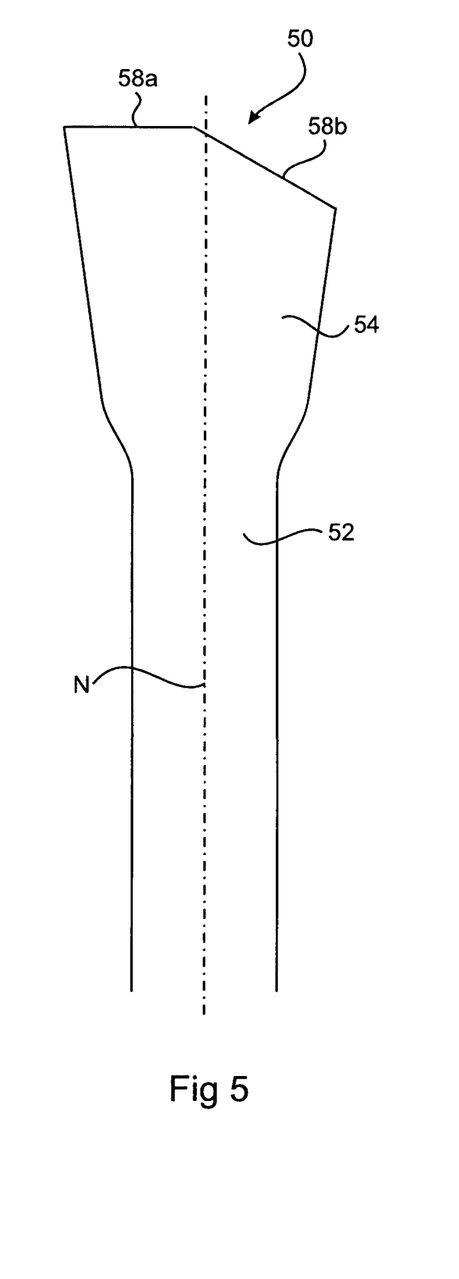
FIG. 5 is a side view of a fourth embodiment of a needle tip in accordance with the present invention.

A fourth embodiment of a needle 50 for a surgical instrument in accordance with the invention, as illustrated in FIG. 5, is also similar to the first embodiment 20 and therefore will not be described again in detail. The needle 50 has a needle body 52 and a spade-shaped needle tip 54. The needle tip 54 has an elliptically shaped mouth, with a major axis larger than an outer diameter of the needle body 52 and a minor axis smaller than the major axis so as to form a spade-shaped tip.

In this embodiment a lip 58 of the mouth of the tip 54 has a first lip portion 58a which is angled in one direction with respect to the tip axis T, and a second lip portion 58b which is angled in the opposite direction with respect to the tip axis T. As in the needle 20 of FIG. 2, the first lip portion 58a of the mouth of the tip is angled with respect to the tip axis T to a different degree than the second lip portion 58b. However in this embodiment, the plane of the first lip portion 58a is angled at about 90° to the tip axis T and the plane of the second lip portion 58b is angled at about 60° to the tip axis T. A line which passes through the points where the two lip portions 58a and 58b meet is slightly offset from the tip axis T. A top plan view of the spade-shaped tip 54 would be similar to that shown in FIG. 2 (b). In other respects the spade-shaped tip 54 may be substantially identical to the tip 24 of the first embodiment and tip 34 of the second embodiment.

Figure 6:
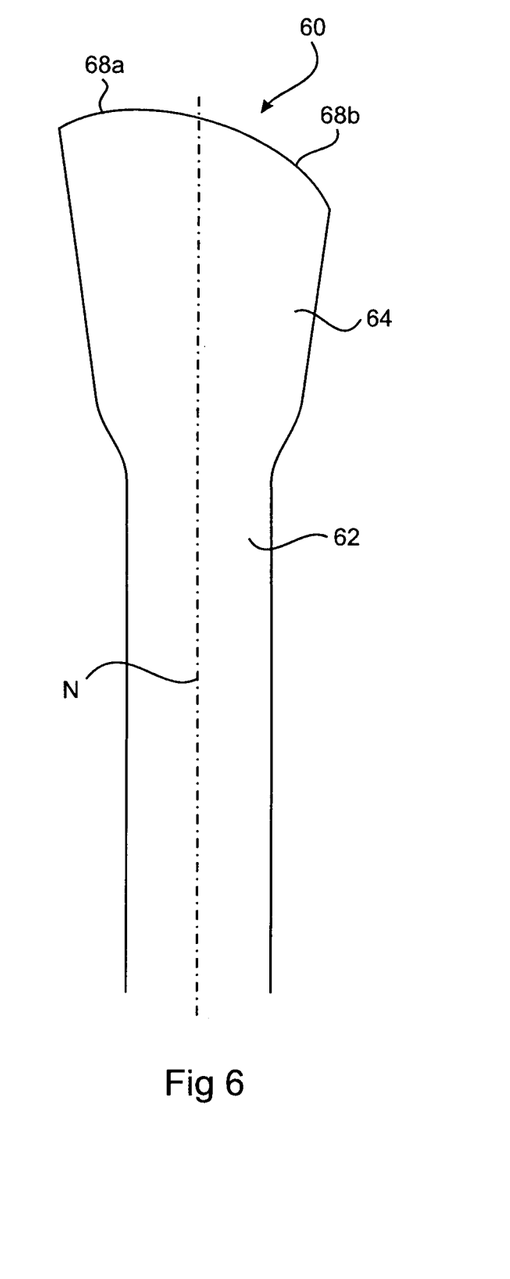
FIG. 6 is a side view of a fifth embodiment of a needle tip in accordance with the present invention; and, FIG. 7 illustrates a typical application of the needle tip according to the invention being used in phacoemulsification.

A fifth embodiment of a needle 60 for a surgical instrument in accordance with the invention, as illustrated in FIG. 6, is also similar to the first embodiment 20 and therefore will not be described again in detail. The needle 60 has a needle body 62 and a spade-shaped needle tip 64. The needle tip 64 has elliptically shaped mouth, with a major axis larger than an outer diameter of the needle body 62 and a minor axis approximately equal to the diameter of the needle body 62 so as to form a spade-shaped tip 64.

As in the needle 40 of FIG. 4, this embodiment of the tip 64 has a lip 68 with a first arcuate lip portion 68a which is angled in one direction with respect to the tip axis T, and a second arcuate lip portion 68b which is angled in the opposite direction with respect to the tip axis T. However, in this embodiment the first and second arcuate lip portions 68a and 68b have respective different degrees of curvature and therefore the lip 68 is not symmetrical about the tip axis T. An end view of the spade-shaped tip 64 would be similar to that shown in FIG. 2 (b). In other respects the spade-shaped tip 64 may be substantially identical to the tip 24 of the first embodiment and tip 34 of the second embodiment.

Figure 7:
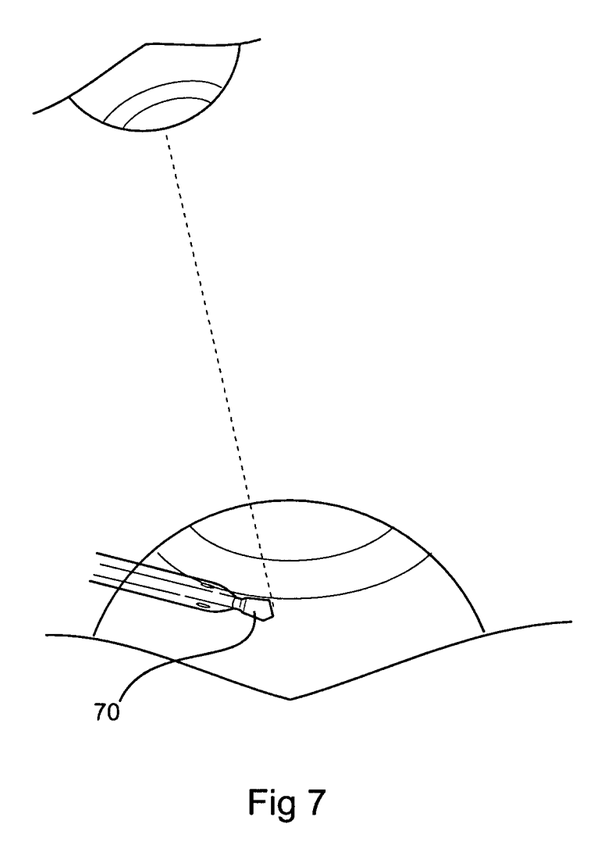

FIG. 7 illustrates schematically an application of a needle tip in accordance with the present invention to phacoemulsification. The spade-shaped tip 70 is inserted into the eye through a small incision until it engages with the lens material. Ultrasonic vibrations are applied to the tip 70 via a phacoemulsification probe (not illustrated) to disintegrate and emulsify the cataract. The anterior chamber and the interior of the bag in which the lens is encapsulated is simultaneously irrigated and aspirated to remove the emulsified cataract fragments. Because of the angled lip portions of the mouth of the tip 70 the surgeon has a clear line of sight of the mouth of the tip and inferior lip where emulsification and aspiration occur.

Trials conducted with torsional ultrasound using designs of elliptical shaped spade-tips, similar to that described, demonstrated that on average a 34% reduction in the energy required for phacoemulsification was achieved compared to the standard bent Kelman needle.

Now that preferred embodiments of the surgical needle tip have been described in detail, it will be apparent that the embodiments provide a number of advantages over the prior art, including the following:
 (i) Improved efficiency in cataract removal compared with a conventional tip (as less energy is used for phacoemulsification because of better acoustic streaming, and better aspiration because of the mouth and lip configuration enhancing the tip fluidics).
 (ii) Reduced trauma from energy side-effects for the patient undergoing the procedure.
 (iii) Less disruption during the procedure due to tip blockage.
 (iv) Good visualisation of the tip mouth and instrument handling ergonomics for the surgeon performing the phacoemulsification procedure.

It will be readily apparent to persons skilled in the relevant arts that various modifications and improvements may be made to the foregoing embodiments, in addition to those already described, without departing from the basic inventive concepts of the present invention. For example, although in each of the described embodiments the spade-shaped tip has a minor axis approximately equal to the diameter of the needle body this is by no means essential to the invention. The minor axis could be larger or smaller than the diameter of the needle body. However it is preferred that it be approximately equal so as to achieve a optimal widening (flaring) of the tip mouth profile without reducing the aspiration flow, or making the needle tip too large. Therefore, it will be appreciated that the scope of the invention is not limited to the specific embodiments described.

The invention claimed is:

1. A needle for a surgical instrument for removal of diseased or unwanted tissue, the needle comprising:
 a hollow elongate needle body having a needle tip at a distal end for cutting tissue, the needle tip being flared in one plane so as to have a width dimension nearer to the needle body smaller than the width dimension further from the needle body and so as to produce a substantially elliptical tip mouth in a second plane substantially orthogonal to a longitudinal axis of the needle body, the tip mouth having a major axis larger than an outer diameter of the needle body and a minor axis smaller than the major axis, the flared tip forming a curved spade-shaped tip, wherein the spade-shaped tip has a central longitudinal tip axis which is substantially aligned with the longitudinal axis of the needle body.

2. A needle as defined in claim 1, wherein the major axis of t le tip mouth is about 1.5 to 2.5 times longer than the minor axis.

3. A needle as defined in claim 1, wherein the minor axis of the tip mouth is approximately equal to the diameter of the needle body.

4. A needle as defined in claim 1, wherein the tip mouth has a lip which is angled with respect to the tip axis.

5. A needle as defined in claim 4, wherein the tip mouth has a first lip portion which is angled in one direction with respect to the tip axis and a second lip portion which is angled in the opposite direction with respect to the tip axis.

6. A needle as defined in claim 5, wherein the first lip portion of the tip mouth is angled with respect to the tip axis to a different degree than the second lip portion.

7. A needle as defined in claim 5, wherein the first and second lip portions of the tip mouth both lie in a respective substantially flat plane.

8. A needle as defined in claim 7, wherein the plane of the first lip portion of the tip mouth is angled at between 90° to 45° to the tip axis. and the plane of the second lip portion of the tip mouth is angled at between 90° to 45° to the tip axis.

9. A needle as defined in claim 8, wherein the plane of the first lip portion is angled at 90° to the tip axis and the plane of the second lip portion is angled at about 60° to the tip axis.

10. A needle as defined in claim 8, wherein the plane of the first lip portion is angled at 60° to the tip axis and the plane of the second lip portion is angled at about 60° to the tip axis.

11. A needle as defined in claim 5, wherein the first and second lip portions of the tip mouth are both substantially arcuate in profile.

12. A needle as defined in claim 11, Wherein the angle of curvature of both the first and second arcuate lip portions is substantially the same.

13. A needle as defined in claim 5, wherein a plane which passes through a line where the two lip portions meet is substantially aligned with the tip axis.

14. A needle as defined in claim 5, wherein the plane which passes through a line where the two lip portions meet is offset from the tip axis.

15. A needle as defined in claim 4, wherein the lip of the tip mouth has a bevelled edge, providing a sharper cutting edge to the lip.

16. A needle as defined in claim 4, wherein the surface of the lip of the tip of the mouth is not smooth, and roughened to create a serrated edge.

17. A needle as defined in claim 4, wherein an internal surface of the tip of the mouth is not smooth and is roughened to the lip of the tip, substantially in the direction of the tip axis.

18. A needle for a surgical instrument for removal of diseased or unwanted tissue, the needle comprising:
a hollow elongate needle body having a needle tip at a distal end for cutting tissue, the needle tip being flared in one plane to produce a substantially elliptical tip mouth in a second plane substantially orthogonal to a longitudinal axis of the needle body, the flared tip forming a curved spade-shaped tip with a central longitudinal tip axis which is substantially aligned with the longitudinal axis of the needle body, the needle body being formed with a neck where it joins the needle tip, wherein the tip mouth has a lip and an internal surface of the needle tip is not smooth and is roughened substantially in the direction of the central longitudinal tip axis of the needle tip so as to form a cutting edge on the lip of the tip mouth.

19. A needle as defined in claim 18, wherein the surface of the lip of the tip mouth is not smooth, and is roughened to create a serrated edge.

20. A needle as defined in claim 19, wherein the internal surface of the needle tip is grooved in the general direction of the tip axis.

21. A needle as defined in claim 20, wherein the grooves extend to the lip of the tip mouth creating a serrated edge to the lip.

22. A needle as defined in claim 21, wherein the grooves extend from the lip of the tip mouth, along the internal surface of the needle tip, to the neck of the needle body.

23. A needle as defined in claim 20, wherein the grooves spiral along the internal surface towards the neck of the needle body.

24. A needle as defined in claim 20, wherein the grooves have a sharp profile on one edge.

25. A needle as defined in claim 20, wherein the grooves have a sharp profile on both edges.

26. A needle as defined in claim 20, wherein the grooves are mostly square or triangular in profile.

27. A needle as defined in claim 20, wherein the grooves are mostly rounded in profile.

28. A needle as defined in claim 20, wherein the grooves are asymmetric about the tip axis.

29. A needle as defined in claim 1, wherein the walls of the needle tip are of a similar thickness to the wall of the needle body.

* * * * *